United States Patent
Hartman et al.

(10) Patent No.: US 11,690,951 B1
(45) Date of Patent: Jul. 4, 2023

(54) IV TUBING CARRIAGE SYSTEM

(71) Applicant: The Cleveland Clinic Foundation, Cleveland, OH (US)

(72) Inventors: Jane Hartman, Berea, OH (US); Nathaniel Hartman, Bexley, OH (US); Nancy Albert, Chesterland, OH (US); Ryan Nowicki, Olmsted Township, OH (US); Zach Hanson, Maple Plain, MN (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 8 days.

(21) Appl. No.: 17/221,244

(22) Filed: Apr. 2, 2021

Related U.S. Application Data

(60) Provisional application No. 63/004,981, filed on Apr. 3, 2020.

(51) Int. Cl.
*A61M 25/02* (2006.01)
*A61M 5/14* (2006.01)

(52) U.S. Cl.
CPC ........ *A61M 5/1418* (2013.01); *A61M 5/1415* (2013.01); *A61M 25/02* (2013.01); *A61M 2025/028* (2013.01); *A61M 2209/084* (2013.01)

(58) Field of Classification Search
CPC .. A61M 5/1418; A61M 5/1415; A61M 25/02; A61M 2025/028; A61M 2209/084; A61M 39/08; A61M 2209/08; A61M 2025/024; A61M 5/1414; A61M 5/1417; A61M 2209/082; A61M 5/14; A61B 50/20; A61B 50/22; A61B 50/24; A61B 50/26; A61B 50/28; A61G 7/0503
See application file for complete search history.

(56) References Cited

U.S. PATENT DOCUMENTS

| | | | |
|---|---|---|---|
| 3,696,920 A | 10/1972 | Lahay | |
| 4,666,111 A | 5/1987 | Schuler | |
| 4,971,271 A | 11/1990 | Sularz | |
| 5,605,534 A * | 2/1997 | Hutchison | A61F 13/041 604/179 |
| 5,728,047 A | 3/1998 | Edoga | |
| 6,387,076 B1 | 5/2002 | Van Landuyt | |
| 6,409,131 B1 * | 6/2002 | Bentley | A61M 5/1415 248/230.1 |
| 6,719,135 B2 | 4/2004 | Armijo | |
| 7,487,791 B1 | 2/2009 | Bradley | |
| 8,974,421 B1 | 3/2015 | Khalaj | |
| 2006/0113432 A1 | 6/2006 | Driskell | |
| 2018/0050149 A1* | 2/2018 | McNeill | A61M 5/1415 |
| 2018/0207416 A1 | 7/2018 | Roddy | |

(Continued)

OTHER PUBLICATIONS

"Hose Tubing Management Clip for CPAP & Oxygen Therapy" Direct Home Medical. https://www.directhomemedical.com—8 pages.

(Continued)

*Primary Examiner* — Bhisma Mehta
*Assistant Examiner* — Phoebe Anne Staton
(74) *Attorney, Agent, or Firm* — Pearne & Gordon LLP

(57) ABSTRACT

A device for supporting IV tubing along a distance and suspending the tubing above the floor includes a support arm and a cradle. The cradle is positioned along a shaft of the support and is configured to receive a length of IV tubing therein.

16 Claims, 5 Drawing Sheets

(56) References Cited

U.S. PATENT DOCUMENTS

2019/0022303 A1    1/2019   Headlee

OTHER PUBLICATIONS

"Beata Clasp Tube Organizer." Medicus Health. https://www.medicus-health.com/beata-clasp-tube-organizer.html 4 pages.

Herriage, et al. "Utilization of an Intravenous Line Lifter Within a Pediatric Oncology Population." Journal of Pediatric Oncology Nursing. 2016, vol. 33(2). pp. 105-110.

NeoGrip Tubing and Cable Holder. Neotech. 2 pages.

NeoHug Utility Device Holder. Neotech. https://www.neotechproducts.com/product/neohug 10 pages.

Tubing Organizers. Surge Cardiovascular. https:/surgecardiovascular.com/product/tubing-organizers 4 pages.

Wahah C-Pap Hose Holder: Health & Personal Care. https://www.amazon.com/WAHAH-Wahah-CPAP-Hose-Holder/dp/B07TBQRTCV/ref=sr_1_1?dchild=1 &keywords=wahah+cpap&qid=1617377463&sr=8-1 8 pages.

TubeCaddy FAQs. Whitney Medical Solutions. https://www.whitneymedicalsolutions.com/med-surg-solutions/tubecaddy-0 4 pages.

ASHE (American Society for Health Care Engineering)—Innovative IV Pump Placement. Mar. 20, 2020. https://www.ashe.org/innovative-iv-pump-placement 2 pages.

\* cited by examiner

IV TUBING CARRIAGE SYSTEM

CROSS REFERENCE TO RELATED APPLICATIONS

This application claims priority to U.S. provisional patent application Ser. No. 63/004,981 filed Apr. 3, 2020, the contents of which are incorporated herein by reference.

TECHNICAL FIELD

This application relates generally to methods and devices to support IV tubing along a distance and suspend the tubing above the floor. More particularly, it relates to a device having a cradle and support arm, wherein the cradle is configured to receive a length of IV tubing therein.

BACKGROUND

Nearly all surgical and intensive care patients have vascular access devices placed to deliver intravenous medications and therapies. In addition, most hospitalized patients require IV fluids and medications as part of their treatment therapy. A vascular access device may be peripherally or centrally inserted into the patient's vein or artery with the end of the catheter hub extending through the skin. A length of IV tubing is connected to the proximal end of the catheter outside of the patient. The opposite end of the tubing then usually is connected to a reservoir of intravenous medication, such as a conventional IV bag. The IV bag typically is hung at an elevated position, and placed in an IV pump relative to where the catheter at the opposite end of the IV tubing enters the patient. This requires the IV tubing to be of some length, often 6 feet or longer.

Moreover, extended lengths of IV tubing often are used for a variety of reasons. For example, it is routine to add length extensions to IV tubing in operating rooms in order to deliver intravenous medications from remotely positioned infusion equipment. Extended length also can be required for ambulation, especially pediatric patients, to permit a suitable freedom of movement. Patients receiving IV therapy often are encouraged or even required to ambulate. To do this they must bring their IV infusions with them, wherein the source bag is hung from a mobile IV pole that rolls on wheels. The IV tubing extending between that source bag and the catheter in the patient can hinder ambulation due to its length.

For example, excessive length may drag on the ground, where it can be stepped on or rolled over by the mobile IV pole. It also can snag on other objects. Either of these conditions can lead to tugging at or even dislodgement of the catheter from the patient, which can be painful and potentially dangerous. Moreover, the weight of extended tubing lengths itself can be a burden even if it is not snagged, again tugging at the catheter in the patient.

It is desirable to reduce the tendency for excessive tubing length to snag or drag along the floor in ambulatory patients. It also is desirable to carry such tubing over extended distances when required in static usage, for example when the location of the patient and the source of intravenous medication are located at a distance from one another.

SUMMARY

In accordance with one aspect of the present disclosure, an IV-tubing carriage system is provided. The carriage system includes a support arm having a flexible shaft, and a cradle defining a tubing pathway adapted to receive and retain a length of IV tubing therein. The cradle is adapted to be detachably held on the flexible shaft.

In accordance with another aspect of the present disclosure, an IV-tubing carriage system is provided. The carriage system includes a support arm having a flexible shaft, and a cradle defining a tubing pathway adapted to receive and retain a length of IV tubing therein. The cradle is formed integrally with the support arm.

In accordance with another aspect of the present disclosure, a method of administering IV therapy to a patient is provided. The method includes delivering an IV drug to a patient from a remote location separated from the patient by an isolation barrier via IV tubing that traverses the isolation barrier. The IV tubing is supported along a pathway from a source of the IV drug to the patient via an IV-tubing cradle suspended above a floor.

DETAILED DESCRIPTION

Figure 1:
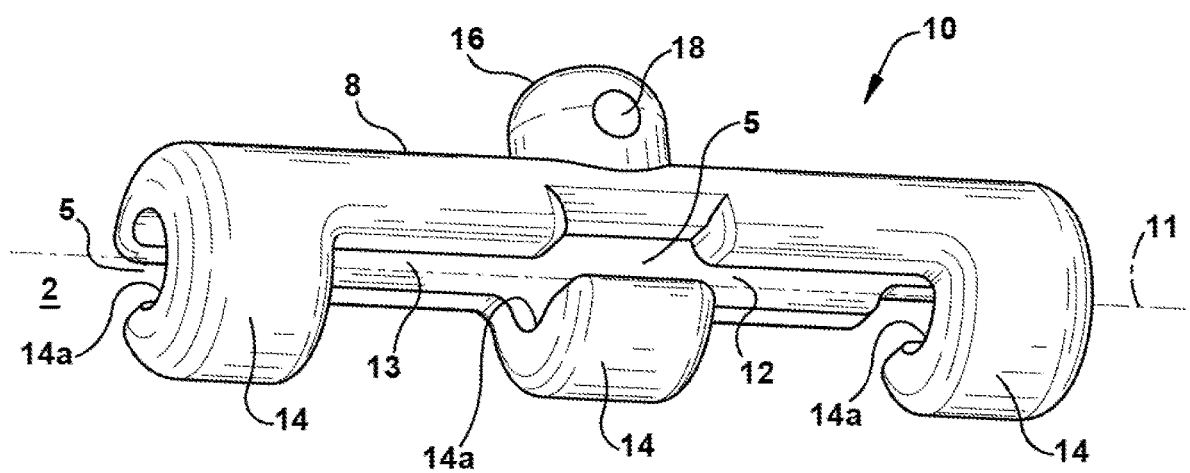
FIG. 1 illustrates a tubing cradle as herein disclosed.

In the embodiment shown in FIG. 1, an IV tubing cradle 10 in the form of an essentially elongate body is shown. The cradle 10 has a tubing pathway 12 running along a longitudinal axis 11 of the body, that receives and accommodates a length of IV tubing when inserted into the cradle 10. The tubing pathway 12 includes a first radiused wall portion 13 defined at an interior of a base portion 8 of the cradle body. The first radiused wall portion 13 extends substantially the length of the cradle 10. Opposite the first radiused wall portion 13 are a plurality of hook elements 14, each cantilevered from the base portion 8 and defining a respective second radiused wall portion 14a opposing the first radiused wall portion 13. Each of the second radiused wall portions 14a cooperates with the opposing first radiused wall portion to define a substantially circular cross section of the tubing pathway 12, at the location of the respective hook element. The hook elements 14 are spaced longitudinally along the length of the cradle 10, preferably so that their respective second radiused wall portions 14a lie in a common arc when viewed end-on along the longitudinal axis 11 (as in FIG. 1a). Viewed along the axis 11, the first radiused wall portion 13 and the opposing second radiused wall portions 14a together define the tubing pathway 12 having a substantially circular cross-section, which extends the length of the cradle 10.

Figure 1A:
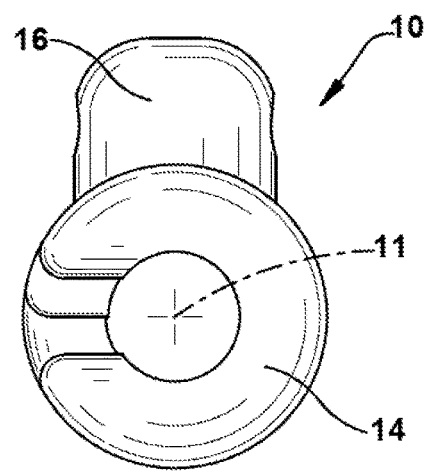
FIG. 1a illustrates a side view of the tubing cradle of FIG. 1.

As seen in FIG. 1, the tubing pathway 12 is open and accessible from outside the cradle 10 between adjacent hook elements 14 thereof. In the illustrated embodiment, the cradle 10 has three hook elements 14, including two at the distal ends of the cradle 10 and one spaced at a midpoint thereof along its length. As also shown in FIG. 1a, the outer hook elements 14 are cantilevered from the base portion 8 of the cradle 10 in a clockwise direction when viewed from a first end 2 of the cradle 10 along the axis 11. Separately, the central hook element 14 is cantilevered from the base portion 8 in a counterclockwise direction when viewed from the first end 2 along the axis 11. In this manner, the hook elements 14 together yield alternately opposing access points 5 into the tubing pathway 12 along the length of the cradle 10. To insert IV tubing therein, portions thereof can be pressed through the access points 5 between distal ends of each of the hook elements 14 and the base portion 8, until those respective portions are fully received in the tubing pathway 12. Because IV tubing is flexible, it can bend easily to be pressed through the alternately opposing access points 5 of the cradle 10.

As seen in FIG. 1, a boss 16 extends from the base portion 8. A through bore 18 is disposed in the boss 16. Preferably, the through bore 18 has a constant diameter and extends along an axis perpendicular to the longitudinal axis 11 of the cradle 10 in a parallel plane, e.g. when viewed from above the boss 18. Though the bore 18 is provided in a boss 16 as shown, the bore 18 can be disposed directly in the base portion 8 if desired, provided there is sufficient thickness to accommodate the bore 18 behind the first radiused wall portion 13. Moreover, the bore 18 need not be a closed bore as illustrated. Rather, if desired it can have a partially open side wall, as if defined between opposing jaw elements that meet along a circumferential point about the bore 18 at their opposing terminal ends (not shown).

Figure 2:
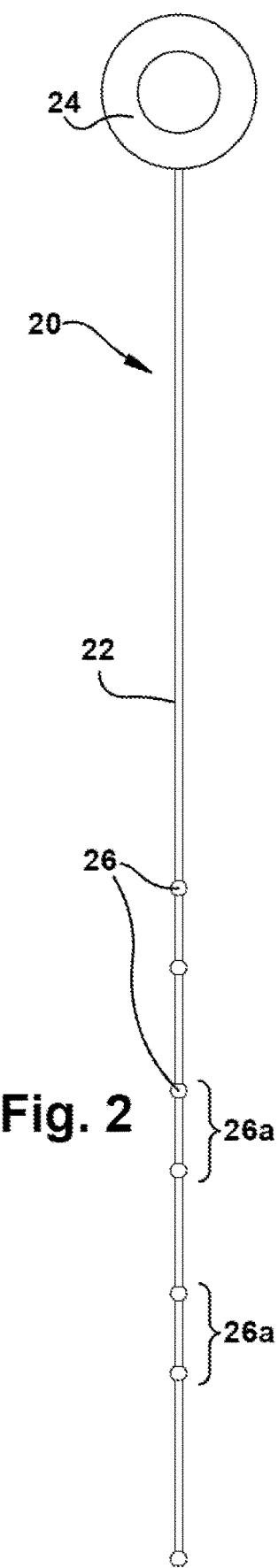
FIG. 2 illustrates an embodiment of a support arm for supporting the tubing cradle of FIG. 1.

However provided, the bore 18 preferably has an interior diameter that is complementary to or adapted to accommodate a shaft 22 of a support arm 20. FIG. 2 illustrates a first embodiment of a support arm 20, wherein a loop 24 is disposed at a first end of the shaft 22. The shaft 22 has a substantially constant diameter, except that a plurality of raised nubs 26 (extending radially from the shaft 22) are disposed at spaced intervals along the shaft length. In FIG. 2, the nubs 26 are provided in cooperating pairs 26a of adjacent nubs as shown. The main diameter of the shaft 22 is small enough that it can slide readily (e.g. complementarily) through the bore 18 in the cradle 10 without interference. The nubs 26, however, increase the effective radius of the shaft 22 where they are located so that the shaft 22 will not readily slide through the bore 18 past a nub 26. Rather, application of an external force will be required to overcome the sliding resistance based on the increased diameter of the nub 26 compared to the bore 18, in order to drive the portion of the shaft 22 where the nub 26 is located through the bore 18. The effective diameter of each nub 26 is not intended to prevent passage through the bore 18. However, it should be large enough such that sliding the shaft 22 through the bore 18 in the location of a nub 26 requires application of an external force beyond merely the force of gravity in order to overcome an interference fit between the nub 26 and the bore 18. Such external force is required to overcome the resulting friction produced by the interference fit, as well as any resistance to elastic deformation in either the nub 26 or the bore 18 to accommodate passage of the former through the latter.

Figure 4:
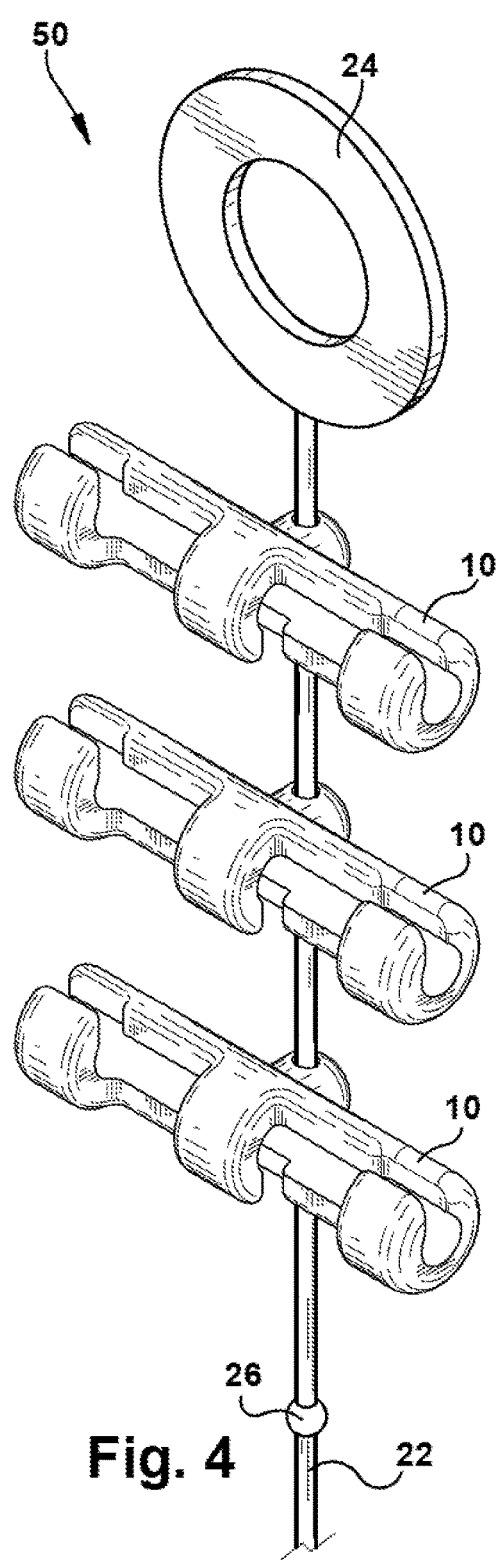
FIG. 4 shows a support arm supporting a plurality of tubing cradles at different elevations along its length.

Returning to FIG. 2, the nubs 26 are provided in pairs 26a as shown. Each pair is spaced apart a distance approximating the height of the boss 16 having the bore 18. In this manner, in use the shaft 22 is inserted through the bore 18 until the first of a nub pair 26a reaches the boss 16, and is then forcibly (though gently) urged further until the leading nub of the pair 26a emerges from the opposite end of the bore 18 on the other side of the boss 16. In this position, the nubs 26 of the given pair 26a will be disposed oppositely and adjacent to the boss 16 at either side thereof. Because each nub 26 presents an obstruction to advancement of the shaft 22 through the bore 18, the cradle 10 is thus securely positioned between the opposing nubs of the pair 26a at a fixed location along the length of the shaft 22. Because there are a plurality of such pairs 26a, the cradle 10 can be adjusted to an optimal or desired elevation along the shaft 22 in a given application. Alternatively, a plurality of individual cradles 10 can be supported at different elevations on the shaft 22 of the same support arm 20. See e.g. FIG. 4. This may be desirable, for example, if multiple IVs are being delivered to the same patient and are thus hung from the same IV pole. It further can be useful if multiple IV tubes for different patients all need to traverse a common path, such that all of them can be supported from above and will not become tangled or fall to the floor. In such circumstances wherein multiple IV tubes are carried by respective cradles 10, the cradles 10 can be individually designated to differentiate them from one another. For example, they may be color coded based on patient, or based on the medication or therapy each carries. These colors can be pre-assigned and standardized to particular therapies so that, for example, total parenteral nutrition (TPN) is always colored yellow and sedation is always colored blue, etc. (or other appropriate colors). By standardizing the colors, different clinicians can know at a glance what sort of therapy is being carried by a particular IV tube. Alternatively, if color coded by patient, then individual clinicians can readily ascertain which tube is being used to provide therapy to his or her patient.

Each support arm 20 can be fitted with one or more cradle(s) 10 to provide a carriage assembly 50, adapted to carry a corresponding number of IV tubes (corresponding to the number of cradles 10) at the location of the assembly 50. As will be appreciated and discussed more fully below, a plurality of carriage assemblies 50 may be desired to support an extended length of IV tubing along a path from a patient to the source where IV therapy is to be administered or controlled by a clinician.

Figure 5:
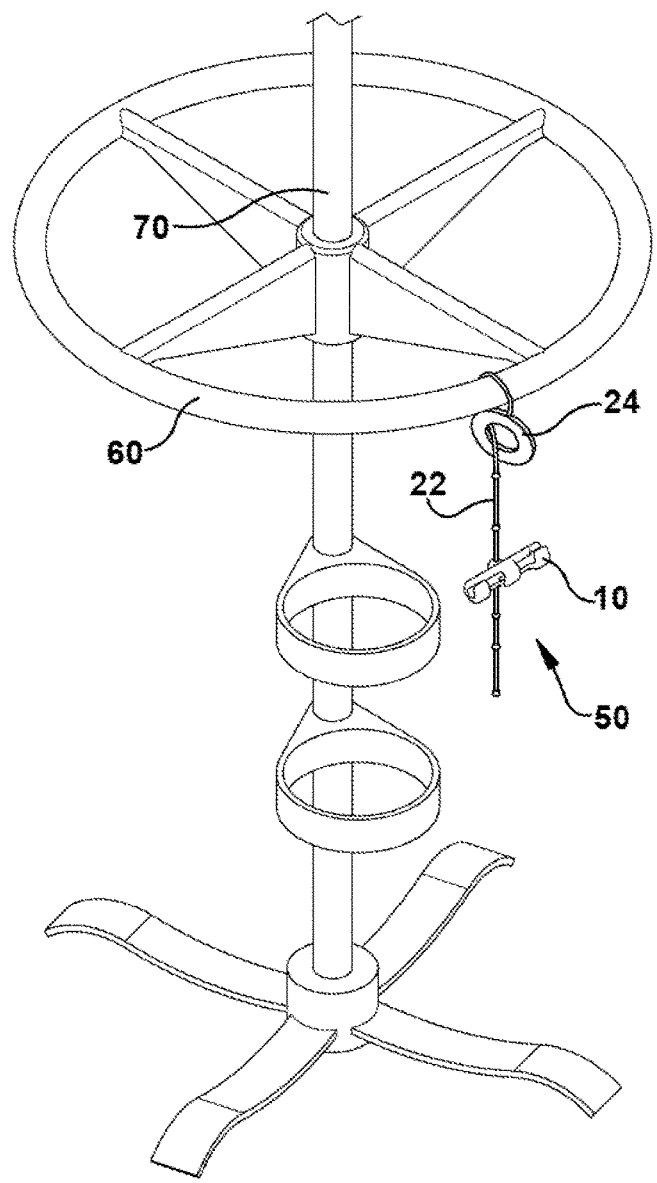
FIG. 5 illustrates a support arm suspended from an IV pole.

As noted above, a loop 24 is disposed at an end of the shaft 22. The loop 24 is effective to suspend the shaft 22 from above, for example, from a conventional IV pole or from any other elevated or overhead support. Alternatively or in addition, and especially when the support arm 20 is made from a flexible or stretchable material such as silicone, the shaft 22 can be flexed and directed through the loop 24 in order to tie the support arm 20 on or to an available support point capable of holding it, for example when no purpose-made IV pole or hook is available. For example, as will be appreciated from FIG. 2, the distal end of the shaft 22 can be flexed and redirected through the loop 24, thus imparting a loop shape to the shaft 22 itself. As illustrated in FIG. 5, the thusly formed shaft loop can be wrapped around an available support point, such as a support ring 60 disposed on an IV pole 70, and then tightened therearound by drawing the shaft 22 further through the loop 24 until taught. Thereafter, one or more cradles 10(s) can be fitted to and suspended from the free end of the shaft 22 as described above. This functionality of the flexible shaft 22 provides a significant degree of freedom for clinicians to identify and select suitable support points as may be available in a given setting, particularly where patient treatment rooms or zones need to be improvised, and suitable purpose-built IV-support posts/poles are not available at desired locations.

Figure 3:
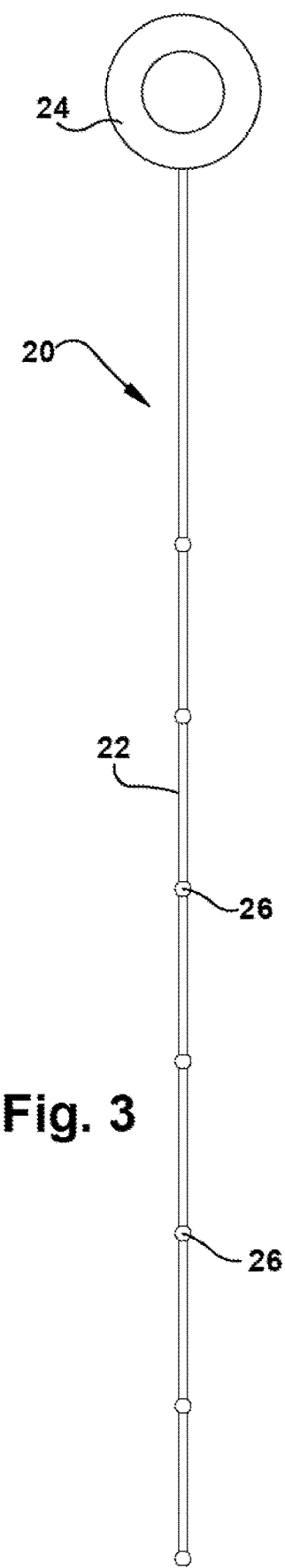
FIG. 3 illustrates a further embodiment of a support arm for supporting the tubing cradle of FIG. 1.

FIG. 3 illustrates a further embodiment of the support arm 20, wherein a plurality of nubs 26 are spaced equidistant along the shaft 22, and not necessarily grouped into pairs as in FIG. 2. Recognizing that the support arm 20 typically will be suspended from its loop 24 located above the shaft 22, a single nub 26 can be used to support a cradle 10 from beneath. No nub 26 typically will be required above the cradle 10 (or boss 16) because gravity will hold the cradle 10 in position against the nub 26 located beneath the bore 18.

Figure 7:
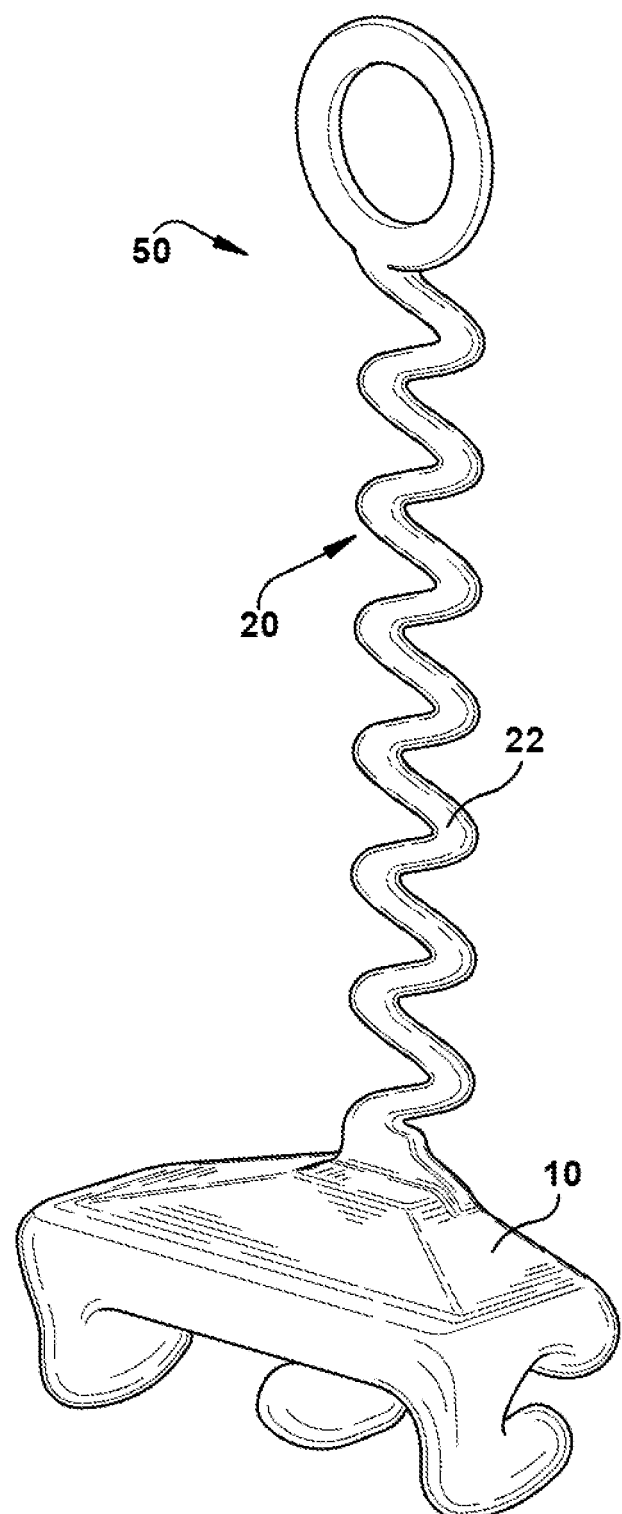
FIG. 7 illustrates a further embodiment wherein the tubing cradle is formed integrally with its support arm.

FIG. 7 illustrates a further embodiment of a carriage assembly 50 wherein the cradle 10 and support arm 20 are formed integral with one another as a single piece. This assembly can be formed, for example, via conventional molding techniques such as injection molding, from flexible plastics, rubbers, or other suitable materials. Alternatively, it can be made via additive manufacturing. Here, the cradle 10 can be substantially as already described in form and features. The support arm 20 can have a length that is at least partially taken up in an accordion or fanfold (zig-zag) pattern at-rest. In this manner, in-use the support arm 20 can accumulate and dampen external-force loads on the IV tubing being held in the cradle 10, which may occur, for example, through the normal cadence of walking or in case of transient movements of the patient. For example, if a patient moves to reach for an object, the support arm 20 can extend from its resting conformation to supply increased length, and thus accommodate the temporary demand for greater slack in the IV tubing. Once the patient returns to his resting position, the support arm 20 elastically recovers to its resting conformation, thus taking up the previously given slack. This embodiment may be preferable for ambulatory patients, particularly those having only one IV, to better accommodate their ambulation.

Each support arm 20 and its associated cradle(s) 10 can form (part of) an IV tubing carriage system to support IV tubing having excess slack or that travels extended distances, at discrete points along the tubing path. As already noted, excess slack to support patient ambulation can be taken up and accumulated in the support arm 20, which can be flexible and elastically stretchable to accommodate transient loads that pull on the tubing. Such a tubing carriage system also can be used to facilitate patient isolation and preserve personal protective equipment (PPE) used by clinicians when caring for patients. Whenever a clinician enters the treatment space of a contagious (or suspected contagious) patient, (s)he is required first to don full PPE, including gown, mask, and gloves. These items of PPE generally are intended to be single use, meaning that they are used for a single patient encounter, and then immediately removed and discarded. Thus, whether changing an IV bag, adjusting the settings of an IV pump, or canceling an alarm on such a pump, to enter the patient-treatment space or room the clinician should don his or her single-use PPE, and then discard it immediately. This can be problematic, particularly during a pandemic or other situation wherein PPE is in short supply. And even absent such circumstances, it is still wasteful of PPE if the sole reason it must be used and discarded is to change out an IV bag or turn off an alarm.

To address this issue, an IV carriage system utilizing the support arm 20 and cradle(s) 10 disclosed herein can be used to move the IV bags, IV pumps, etc. that supply or regulate intravenous medication (e.g. hanging from an IV pole) outside of the treatment space/room, remote from the patient. That is, one or plurality of carriage assemblies 50 can be hung from available support points along the path between the patient and the remote location outside the treatment space in order to support the IV tubing along that distance and suspend it above the floor and out of the way of caregivers, other equipment or machinery, or other traffic. If desired, such carriage assemblies 50 can be hung from strategically positioned IV poles between the patient and the remote location. Alternatively, they can be hung from any available support point(s) as may be available or even improvised along that path. Such IV carriage systems are illustrated schematically in FIG. 6, wherein carriage assemblies 50 as herein disclosed are hung from a hook or other suitable structure in order to support an extended length of IV tubing. That tubing extends from a patient in bed within an isolation zone (such as an ICU room), through that zone until it exits that zone, e.g. through an isolation barrier such as a wall, plastic sheeting, curtain or other conventional barrier via a doorway, passageway or other opening adapted or capable to accommodate passage of the IV tubing, until it reaches a location where the medication supplied via that tubing and IV pump 80 can be administered or regulated. In this manner, when IV medication needs to be changed, or for example when an alarm condition occurs at or adjacent to a source of the IV medication (e.g. the IV pump 80 or other IV infusion equipment), or when the source (such as an IV bag) itself needs replaced, so long as the condition does not require direct patient engagement the clinician can attend to it outside the patient isolation zone, and thus need not don PPE as otherwise would be required to enter that zone.

Figure 6:
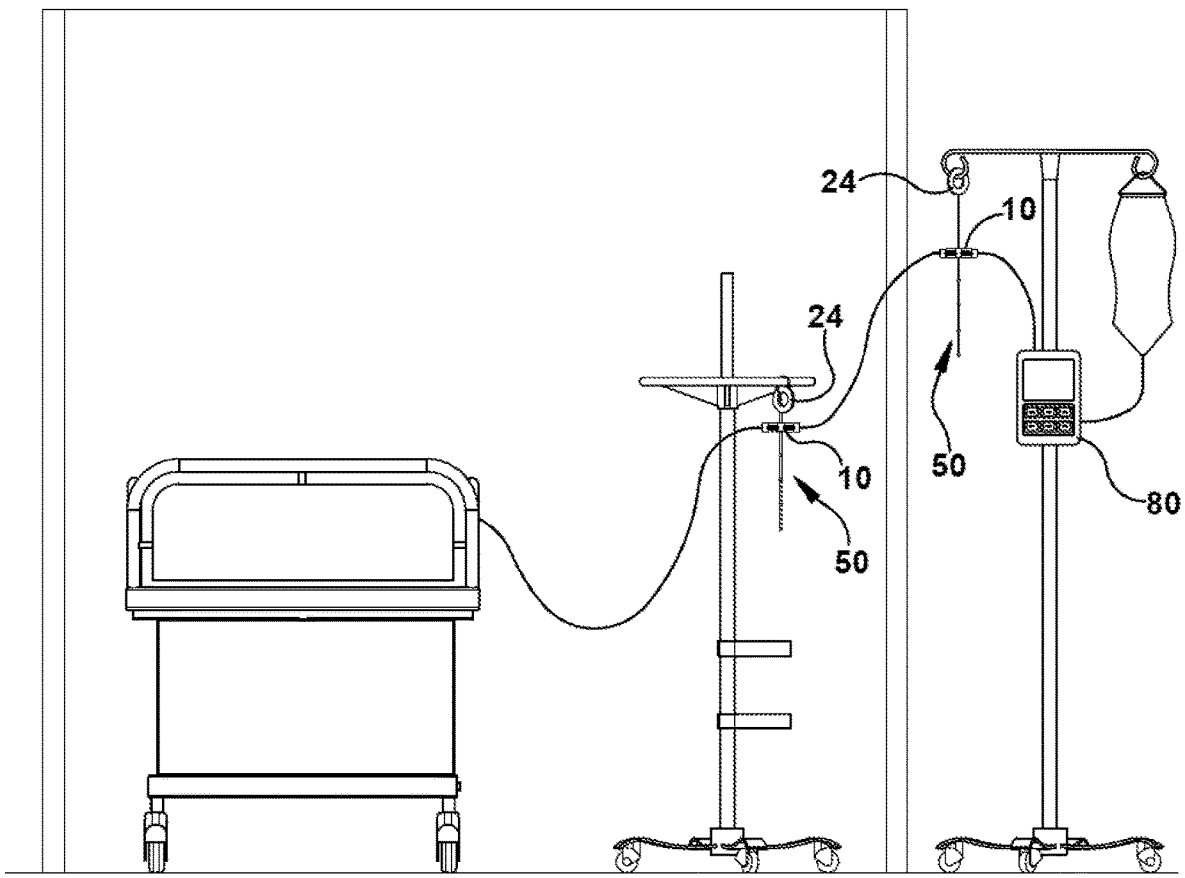
FIG. 6 illustrates carriage assemblies as herein disclosed to support IV tubing an extended distance between a patient bed in isolation and a remote location wherein a clinician may administer IV therapy without being exposed to a patient.

In FIG. 6, two carriage assemblies 50 are shown supporting the IV tubing between the patient and the IV bag/source. However, any number of such assemblies 50 can be utilized, at different locations along the path between the patient and the source if appropriate to provide support to the tubing across that distance. As noted above, such assemblies 50 can be hung from any available support point. As shown in FIG. 6, one or more mobile or stationary IV poles can be provided at strategic locations from which to hang carriage assemblies 50 to support the IV tubing along its length.

Although the invention has been described with respect to select embodiments, it shall be understood that the scope of the invention is not to be thereby limited, and that it instead shall embrace all modifications and alterations thereof coming within the spirit and scope of the appended claims.

What is claimed is:

1. An IV-tubing carriage system comprising a support arm having a flexible shaft and a cradle defining a tubing pathway adapted to receive and retain a length of IV tubing therein, the flexible shaft being configured to support the cradle at a plurality of predefined locations, the cradle being a separate component from the flexible shaft, the cradle being adapted to be detachably held on the flexible shaft at one of the plurality of predefined locations.

2. The carriage system of claim 1, the cradle being reversibly re-positionable between the plurality of predefined locations along the flexible shaft.

3. The carriage system of claim 1, the cradle comprising a base portion having a first wall portion, and a hook element cantilevered from the base portion and defining a second wall portion, the first and second wall portions opposing one another and together at least partially defining the tubing pathway of the cradle.

4. The carriage system of claim 3, the first and second wall portions each being radiused.

5. The carriage system of claim 3, the first wall portion extending substantially a length of the cradle.

6. The carriage system of claim 3, comprising a plurality of the hook elements cantilevered from the base portion, each defining a respective said second wall portion opposing the first wall portion, a plurality of access points for insertion of the IV tubing into the tubing pathway being defined between distal ends of the respective hook elements and the base portion.

7. The carriage system of claim 6, the plurality of access points being alternately opposed along a length of the cradle.

8. The carriage system of claim 1, the flexible shaft having a plurality of raised nubs disposed along a length of the shaft and corresponding to said plurality of predefined locations, the cradle further comprising a bore adapted to receive the flexible shaft therethrough, the plurality of raised nubs presenting an interference fit for sliding the flexible shaft through the bore such that the cradle can be supported by one nub of the plurality of raised nubs on the flexible shaft.

9. The carriage system of claim 8, wherein the bore is disposed in a boss of the cradle.

10. The carriage system of claim 9, wherein a pair of nubs of the plurality of nubs are spaced apart a distance approximating a height of the boss, the cradle being reversibly held therebetween.

11. The carriage system of claim 8, the flexible shaft reversibly supporting a plurality of the cradles along its length at respective nubs of the plurality of nubs thereof.

12. The carriage system of claim 1, the flexible shaft further comprising a loop at a first end thereof that is at least large enough to accommodate the flexible shaft therethrough.

13. The carriage system of claim 1, the support arm being elastically stretchable.

14. A method of administering IV therapy to a patient, comprising delivering an IV drug to the patient from a remote location separated from the patient by an isolation barrier via IV tubing that traverses the isolation barrier, the IV tubing being supported along a pathway from a source of the IV drug to the patient via the IV-tubing carriage system of claim 1 suspended above a floor.

15. The method of claim 14, wherein the flexible shaft has a plurality of raised nubs disposed along its length and corresponding to said plurality of predefined locations, the cradle comprising a bore and receiving the flexible shaft therethrough, the plurality of raised nubs presenting an interference fit for sliding the flexible shaft through the bore such that the cradle is supported by one nub of the plurality of raised nubs on the flexible shaft.

16. An IV-tubing carriage system comprising a support arm having a flexible shaft and a cradle defining a tubing pathway adapted to receive and retain a length of IV tubing therein, the flexible shaft being configured to support a plurality of said cradles, respectively, at a plurality of predefined locations along its length, wherein each said cradle is adapted to be detachably held on the flexible shaft at one of the plurality of predefined locations.

* * * * *